United States Patent [19]

Cusic et al.

[11] B 3,985,730

[45] Oct. 12, 1976

[54] 5-ALKYL-10-(AMINOCARBONYL/AMINOMETHYL/CYANO)-10,11,-DIHYDRO-5H-DIBENZ[b,f]AZEPINE-10-ALKANAMINES

[75] Inventors: John W. Cusic, Skokie; Charles R. Ellefson, Chicago, both of Ill.

[73] Assignee: G. D. Searle & Co., Chicago, Ill.

[22] Filed: Nov. 4, 1974

[21] Appl. No.: 520,256

[44] Published under the second Trial Voluntary Protest Program on January 13, 1976 as document No. B 520,256.

[52] U.S. Cl. ............................ 260/239 D; 424/244
[51] Int. Cl.² ....................................... C07D 223/22
[58] Field of Search ............................... 260/239 D

[56] References Cited

UNITED STATES PATENTS

R27,622  4/1973  Schindler et al. ............... 260/239 D

FOREIGN PATENTS OR APPLICATIONS 1,355,948  4/1972  France ............................ 260/239 D

*Primary Examiner*—Richard J. Gallagher
*Assistant Examiner*—D. B. Springer
*Attorney, Agent, or Firm*—John M. Brown

[57] ABSTRACT

Preparation and the antiarrhythmic and antimicrobial properties of 5-alkyl-10-(aminocarbonyl/aminomethyl/cyano)-10,11-dihydro-5H-dibenz[b,f]azepine-10-alkanamines and equivalent salts are disclosed.

15 Claims, No Drawings

5-ALKYL-10-(AMINOCARBONYL/AMINOMETHYL/CYANO)-10,11-DIHYDRO-5H-DIBENZ[b,F]AZEPINE-10-ALKANAMINES

This invention relates to 5-alkyl-10-(aminocarbonyl/aminomethyl/cyano)-10,11-dihydro-5H-dibenz[b,f]azepine-10-alkanamines, and to processes for the preparation thereof. More particularly, this invention provides new, useful, and unobvious amines of the formula

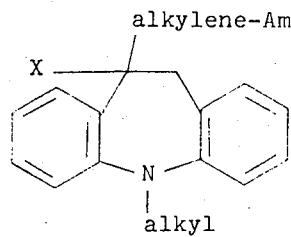

wherein X represents aminocarbonyl, aminomethyl, or cyano and Am represents an amino radical.

Am in the foregoing formula for compounds of this invention subsumes both the primary amino radical, $-NH_2$, and secondary and most advantageously tertiary amino radicals resulting from the substitution of one and two alkyl radicals, respectively, for hydrogen therein — especially lower alkyl radicals, such as methyl, ethyl, propyl, isopropyl, butyl, isobutyl, sec.-butyl, tert.-butyl, pentyl, neopentyl, hexyl, isohexyl, heptyl, and like monovalent, saturated, acyclic, straight- or branched-chain, hydrocarbon groupings having the formula $$-C_nH_{2n+1}$$

wherein $n$ represents a positive integer less than 8. The alkyl groupings present when Am designates a tertiary amino radical may be either discrete, thus

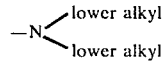

or they may be joined together directly or through oxygen or a second nitrogen atom to compose cyclic amino radicals optimally but not necessarily exclusively comprising at least four or as many as eight carbon atoms. Illustrative of the cyclic amino radicals contemplated by Am are pyrrolidino, methylpyrrolidino, dimethylpyrrolidino, trimethylpyrrolidino, piperidino, methylpiperidino, dimethylpiperidino, methylethylpiperidino, morpholino, piperazino, methylpiperazino, ethylpiperazino, and like 5- or 6-membered heterocyclic groupings. The terminal "ino" in the radical names set forth denotes attachment of the radicals thus characterized by a nitrogen. Also within the purview of Am in the introductory formula for compounds of this invention are N-alkyl-N-benzylamino groupings, preferably those wherein the alkyl constituent is of lower order as hereinbefore defined.

The 5-alkyl contemplated by the introductory formula is, again, preferably a lower alkyl; and the alkylene called for by the formula is likewise preferably of lower order. Illustrative of such alkylenes are methylene, ethylene, trimethylene, propylene, tetramethylene, 1,1-dimethylethylene, pentamethylene, 2,2-dimethyltrimethylene, and like bivalent, saturated, acyclic, straight- or branched-chain, hydrocarbon groupings having the formula $$-C_nH_{2n}-$$

wherein $n$ represents, as above, a positive integer less than 8.

Equivalent to the aforesaid amines for the purposes of this invention are corresponding non-toxic acid addition salts thereof having the formula

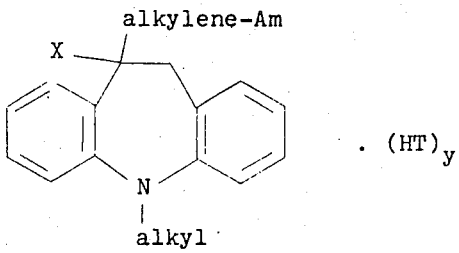

wherein X and Am have the meanings previously assigned; T represents one equivalent of an anion — for example, chloride, bromide, iodide, nitrate, phosphate, sulfate, sulfamate, methyl sulfate, ethyl sulfate, benzenesulfonate, toluenesulfonate, acetate, lactate, succinate, maleate, tartrate, citrate, gluconate, ascorbate, benzoate, cinnamate, or the like — which, in combination with the cationic portion of a salt aforesaid, is neither biologically nor otherwise incompatible; and y represents a positive integer less than 5, its precise value being dependent upon the number of basic nitrogens involved in salt formation.

The compounds of this invention are useful by reason of their valuable biological properties. Thus, for example, they are antiarrhythmic and antimicrobial.

The antiarrhythmic utility of the instant compounds is evident from the results of a standardized test for their capacity to slow the ventricular tachycardia induced by aconitine in the isolated rabbit heart. The procedure is essentially that described by Lucchesi [J. Pharmacol. Exp. Therap., 137, 291 (1962)], modified in certain particulars as follows: Hearts are obtained from adult albino rabbits of either sex and perfused in apparatus modeled after that devised by Anderson and Craver [J. Pharmacol. Exp. Therap., 93, 135 (1948)]. Composition of the perfusion solution is the same as Lucchesi's, but the volume is increased to 211 ml and the temperature lowered to 28°. Aconitine (ordinarily as the nitrate) is administered as soon as the heart beat is regular and the EKG pattern normal, the dose being so selected as to at least double the rate. Typically, 0.05 ml of 0.1% aconitine nitrate in physiological saline is injected. EKG's are recorded at 5-minute intervals after onset of ventricular tachycardia until two successive readings show stabilization of the rate. Perfusate collected during this time is discarded and replaced with fresh solution q.s. 200 ml. Promptly following stabilization, 2 mg of compound dissolved or suspended in 1 ml of physiological saline is mixed with the perfusion solution; 10 minutes later a like amount is introduced, followed after a further 10 minutes by double the first amount. Final concentration of compound in the perfusion solution is thus 40 mg per l. Recording of EKG's is continued at 5-minute intervals throughout this time and for 10 minutes thereafter. A compound is considered antiarrhythmic if, at any time during the 30 minutes immediately following initial administration in more than half of a minimum of 2 tests, it reduces by at least 50% the rate recorded 10 minutes after onset of tachycardia. Illustrative, but not limiting, is the finding that the products of Examples 3B, 11B, and 16B hereinafter were antiarrhythmic in this test.

The antiarrhythmic utility of the instant compounds is further evident from the results of a standardized test for their capacity to counteract the ventricular ectopic arrhythmia induced by a two-stage ligation of the anterior descending branched of the left coronary artery in the intact dog. The ligation technique, performed substantially as described by A. Sidney Harris in Circulation 1, 1318 (1950), involves anesthetizing the animal with 32.5 mg per kg of sodium pentobarbital, administered intravenously, and maintaining respiration mechanically via tracheal intubation while the chest cavity is opened on the left side at the fourth interspace and (1) the artery is tied against a 20-gage hypodermic needle at a point approximately 1 cm from the artrial tip, (2) the needle is removed, (3) 30 minutes later the artery is completely occluded by ligation, and (4) the opening is closed. On the first post-operative day, if an EKG reveals 75% ectopic beats, 5 mg per kg of compound dissolved or suspended at a concentration of 1% in aqueous 0.9% sodium chloride or other physiologically inert vehicle is administered during 5 minutes via a scalp-vein needle placed in the cephalic vein. EKG's are recorded at 2.5-minute intervals, and the drug dose is repeated at 15-minute intervals until there is either a reduction in ectopic beats amounting to at least 25% and lasting for a minimum of 10 minutes or a total drug dose of 20 mg per kg has been administered. A compound is considered antiarrhythmic in this test if the aforesaid reduction is induced in more than half of at least 2 dogs. Further by way of illustration only, the product of Example 11B was antiarrhythmic at 12.5 mg per kg in this test.

The antiarrhythmic utility of the instant compounds is still further evident from the results of a standardized test for their capacity to restore normal sinus rhythm in dogs pretreated with sufficient ouabain to induce ventricular tachycardia. The test animals are anesthetized with 37.5 mg per kg of sodium pentobarbital; an endotracheal tube is emplaced to facilitate breathing; Lead II EKG's are monitored; and drugs are introduced via a cannula in the left femoral vein, each dose being washed in with 1 ml of a 0.1% solution of heparin in aqueous 0.9% sodium chloride. Heart beats per minute are calculated by multiplying the number of QRS patterns during a 6-second period by 10. Initially, a 40-mcgm-per-kg dose of the ouabain solution is administered after 30 minutes if the heart beat remains normal, or after 45 minutes if arrhythmic at the 30-minute mark but normal 15 minutes later. A still further 10-mcgm-per-kg dose of the ouabain solution is administered 15 minutes after the 20-mcgm-per-kg dose if the heart beat is normal, or 30 minutes after the 20-mcgm-per-kg dose if arrhythmia 15 minutes thereafter has reverted to normal. Additional 10-mcgm-per-kg doses of the ouabain solution are administered at 15-or-30-minute intervals as above if necessary, the total ouabain dosage being the minimum amount necessary to induce ventricular tachycardia which is self-sustaining for at least 15 minutes. To such animals, the compound to be tested is administered in a vehicle consisting of aqueous 0.9% sodium chloride, 95% propylene glycol, or other physiologically inert vehicle at a concentration of 1%. The initial dose of compound is ordinarily 5 mg per kg. A compound is considered antiarrhythmic in this test if it restores normal sinus rhythm persisting for 15 minutes in more than half of a minimum of 2 animals at a dose of 20 mg per kg or less. Doses larger than 5 mg per kg are ordinarily administered in 5-mg-per-kg increments spaced approximately 15 minutes apart. Again by way of illustration only, the product of Example 11B was antiarrhythmic at 15 mg per kg in this test.

The antimicrobial properties of the compounds of this invention include antibacterial, antiprotozoal, anthelmintic, antifungal, and antialgal activity.

The antibacterial utility of the instant compounds is evident from the results of standardized tests for their capacity to inhibit the growth of *B. subtilis* and *Erwinia sp.* described in U.S. Pat. No.. 3,682,951. For instance, the product of Example 3B hereinafter was found active at a concentration of 100 mcgm per ml in these tests, as also in the following standardized test for activity vis-a-vis the anaerobic bacterium, *Propionibacterium acnes* ATCC 6919. In this test, fluid thioglycollate medium (manufactured by Baltimore Biological Laboratories or Difco) is prepared as recommended by the manufacturer, sterilized, and innoculated with *Propionibacterium acnes* ATCC 6919 q.s. 1,000,000 cells per ml, determined spectrophotometrically. Meanwhile, compound is heated in sterile distilled water at a concentration of 1,000 mcgm per ml for 20 minutes at 80°C. This compound preparation is serially diluted and mixed with sufficient inoculated medium to afford concentrations of 100, 10, 1, and 0.1 mcgm of compound per ml. The mixtures thus obtained are incubated anaerobically for 20–24 hours at 37 °C. and then examined grossly for growth of the organism. Controls are provided by concurrent incubations identical with the above except that (1) reference standard (4.3, 0.43, 0.043, and 0.0043 mcgm per ml of streptomycin sulfate and 6667, 667, 67, and 7 units of potassium penicillin G) are substituted for compound and (2) neither compound nor reference standard is present. Compounds are considered active if, at the maximum concentrations tested, no growth of organism is observed and no aberrancy is apparent in respect of the controls. Potency is expressed as the miminum concentration at which a compound is active.

The antiprotozoal utility of the instant compounds is evident from the results of a standardized test for their capacity to inhibit the growth of *Trichomonas vaginalis* described in U.S. Pat. No. 3,483,192; and their anthelmintic, antifungal, and antialgal activity is evident from the results of the tests for their capacity to inhibit the growth of *Turbatrix aceti*, *Trichophyton mentagrophytes*, *Verticillium albo-atrum* and *Chlorella vulgaris* described in U.S. Pat. No. 3,682,951. Thus again for instance, the product of Example 3B hereinafter was found active at a concentration of 1,000 mcgm per ml in these tests.

Those skilled in the art will recognize that observations of activity in standardized tests for particular biological effects are fundamental to the development of valuable new drugs, both veterinary and human. Distinct from such applications, antialgal compounds are adapted to the conditioning of boiler feed water and the like.

Preparation of the compounds of this invention proceeds by heating a solution of 5H-dibenz[b,f]azepine in chloroform with an alkanoyl chloride (as, for example, 1-oxopropyl or 2-methyl-1-oxopropyl chloride), 10,11- dibrominating the resultant 5-alkanoyl-5H-dibenz[b,f]azepine by contacting it in chloroform solution with bromine, dehydrobrominating the compound thus obtained by heating it with N-butylbutanamine to give 5-alkanoyl-10-bromo-5H-dibenz[b,f]azepine, reducing the carbonyl therein via contact in cold tetrahydrofuran solution with aluminum hydride formed in situ from lithium tetrahydroaluminate(1-) and sulfuric acid in tetrahydrofuran according to the procedure of Brown and Yoon [J. Amer. Chem. Soc., 88, 1464 (1966)], replacing bromo with cyano in the resultant 5-alkyl compound by heating the compound in N,N-dimethylformamide with copper(I) cyanide, and reducing the 10,11-double bond in the 5-alkyl-5H-dibenz[b,f]azepine-10-carbonitrile thus obtained by heating the compound with sodium tetrahydroborate(1-) in ethanol, affording a compound of the formula

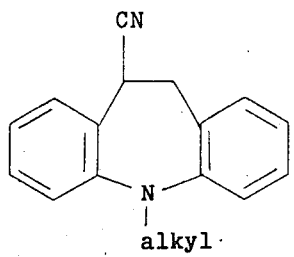

As an exception to the foregoing procedure, 10,11-dihydro-5-methyl-5H-dibenz[b,f]azepine-10-carbonitrile eventuates by heating 5H-dibenz[b,f]azepine with ethyl chloroformate in dichloromethane, thereby obtaining ethyl 5H-dibenz[b,f]azepine-5-carboxylate, and then — as described above — consecutively 10,11-dibrominating, dehydrobrominating, contacting with aluminum hydride formed in situ from lithium tetrahydroaluminate(1-) and sulfuric acid in tetrahydrofuran (whereby the 5-ethoxycarbonyl is reduced to methyl), replacing bromo with cyano, and 10,11-dihydrogenating.

By heating 5-alkyl-10,11-dihydro-5H-dibenz[b,f]azepine-10-carbonitriles, in the presence of sodium hydride and using tetrahydrofuran as the reaction medium, with aminoalkyl chlorides of the formula Am—alkylene—Cl wherein Am is defined as above, the 5-alkyl-10-cyano-10,11-dihydro-5H-dibenz[b,f]azepine-10-alkanamines of this invention are obtained. However, a preferred means to products of the introductory formula wherein Am represents alkylamino is by debenzylation of corresponding N-alkyl-N-benzylamines via low pressure hydrogenation in ethanol, using palladium on carbon as a catalyst.

By heating 5-alkyl-10-cyano-10,11-dihydro-5H-dibenz[b,f]azepine-10-alkanamines with potassium hydroxide in aqueous ethanol the 5-alkyl-10-aminocarbonyl-10,11-dihydro-5H-dibenz[b,f]azepine-10-alkanamines of this invention are obtained. Alternatively, substitution of concentrated sulfuric acid for the potassium hydroxide in aqueous ethanol affords the latter product.

By contacting 5-alkyl-10-(aminocarbonyl/cyano)-10,11-dihydro-5H-dibenz[b,f]azepine-10-alkanamines with aluminum hydride in tetrahydrofuran the 5-alkyl-10-aminomethyl-10,11-dihydro-5H-dibenz[b,f]azepine-10-alkanamines of this invention are obtained.

Conversions of the bases of this invention to corresponding acid addition salts is accomplished by simple admixture with four or fewer equivalents, as indicated, of any of various inorganic and strong organic acids, the anionic portion of which conforms to T as hereinabove defined. The salts, in turn, are converted to corresponding bases by contacting with excess alkali.

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set forth, temperatures are given in degrees centigrade and relative amounts of materials in parts by weight, except as otherwise noted.

EXAMPLE 1

A. To a mixture of approximately 131 parts of 5H-dibenz[b,f]azepine with 775 parts of chloroform is very slowly added, with stirring, 80 parts of acetyl chloride. The resultant mixture is heated at the boiling point under reflux with stirring for 4 hours, then cooled, consecutively washed with aqueous 5% sodium hydroxide and water, dried over magnesium sulfate, and stripped of solvent by vacuum distillation. The residual oil crystallizes from hexane as a colorless solid. The product thus isolated is 5-acetyl-5H-dibenz[b,f]azepine.

B. To a solution of 155 parts of 5-acetyl-5H-dibenz[b,f]azepine in 900 parts of chloroform at 0°–5° is very slowly added a solution of approximately 107 parts of bromine in 200 parts of chloroform. The resultant mixture is stirred at ambient temperatures for 1½ hours, then mixed with decolorizing charcoal and filtered. From the filtrate, on refrigeration at −20°, 5-acetyl-10,11-dibromo-10,11-dihydro-5H-dibenz[b,f]azepine separates as a light yellow solid which is isolated by filtration and dried in air.

C. A mixture of 220 parts of 5-acetyl-10,11-dibromo-10,11-dihydro-5H-dibenz[b,f]azepine and 240 parts of N-butylbutanamine is heated with stirring at 90°–95° until exothermy occurs, and for 1 hour thereafter. The resultant mixture is extracted with ether; and the ether extract is consecutively washed with 5% hydrochloric acid and water, dried over magnesium sulfate, and stripped of solvent by vacuum distillation. The residue is consecutively washed with cold ether and hexane, then dried in air. The product thus isolated is 5-acetyl-10-bromo-5H-dibenz[b,f]azepine melting at 100°–102°.

D. To 275 parts of a vigorously-stirred 3½% solution of lithium tetrahydroaluminate(1-) in tetrahydrofuran at 0°–5° is slowly added 8 parts of concentrated sulfuric acid. The resultant mixture is stirred at 0°–5° for 1 hour, whereupon a solution of approximately 63 parts of 5-acetyl-10-bromo-5H-dibenz[b,f]azepine in 135 parts of tetrahydrofuran is stirred in during 30 minutes, producing a yellow color. The mixture thus obtained is stirred at 0°–5° for 30 minutes, whereupon a mixture of 20 parts of water and 35 parts of tetrahydrofuran, followed first by 40 parts of aqueous 25% sodium hydroxide and finally by 30 parts of water, are consecutively introduced. Insoluble solids are thereupon filtered out and washed with hot tetrahydrofuran, and the washings are combined with the filtrate. The resultant solution is dried over magnesium sulfate and stripped of solvent by vacuum distillation. The residual yellow solid, recrystallized from 2-propanol, affords 10-bromo-5-ethyl-5H-dibenz[b,f]azepine melting at approximately 147.5°–148.5°.

E. A mixture of approximately 47 parts of 10-bromo-5-ethyl-5H-dibenz[b,f]azepine and 29 parts of copper(I) cyanide in 350 parts of N,N-dimethylformamide is heated at the boiling point under reflux with stirring for 1½ hours, then cooled to room temperature and poured into approximately 1,200 parts of concentrated ammonium hydroxide. The resultant mixture is extracted with dichloromethane; and the extract is consecutively washed with 4% hydrochloric acid, water, a saturated aqueous solution of sodium bicarbonate, and water, whereupon it is dried over magnesium sulfate and then stripped of solvent by vacuum distillation. The residual oil crystallizes on cooling. Recrystallized from ethanol, it affords gold-colored 5-ethyl-5H-dibenz[b,f]-azepine -10-carbonitrile melting at 144°–146.5°.

F. To a solution of approximately 49 parts of 5-ethyl-5H-dibenz[b,f]azepine-10-carbonitrile in 1,600 parts of absolute ethanol at 70°–75° is added, portionwise with stirring, 76 parts of sodium tetrahydroborate (1-). When the addition is conplete, the reaction mixture is maintained at 70°–75° with stirring for a further 1 ½ hours, whereupon it is cooled and solvent is then removed by vacuum distillation. Approximately 2,000 parts of water is mixed with the residue. Insoluble solids are filtered out, washed on the filter with water, dried in air, and recrystallized from ethanol to give 5-ethyl-10,11-dihydro-5H-dibenz[b,f]azepine-10-carbonitrile as a yellow solid melting at 127°–129°.

G. A solution of 744 parts of 5-ethyl-10,11-dihydro-5H-dibenz[b,f]azepine-10-carbonitrile in approximately 6,800 parts of tetrahydrofuran is added to 200 parts of a 57% dispersion of sodium hydride in white oil. The resultant mixture is heated at the boiling point under reflux with stirring for 1 hour, whereupon a solution of 356 parts of 2-chloro-N,N-dimethylethanamine in approximately 400 parts of xylene is stirred in. Thin layer chromatography, with neutral alumina as the adsorbent and 10% ethyl acetate in benzene as the developing solvent, is used to monitor the reaction which ensures as reflux with stirring is continued overnight, sufficient additional sodium hydride dispersion being introduced to insure that 5-ethyl-10,11-dihydro-5H-dibenz[b,f]azepine-10-carbonitrile is no longer detectable. The reaction mixture is thereupon cooled to room temperature, and water is slowly added until the evolution of hydrogen ceases. Solvent is then removed by vacuum distillation, and the residue is partitioned between ether and water. The ethereal phase is dried over magnesium sulfate and stripped of solvent by vacuum distillation. The residue is 10-[2-(dimethylamino)-ethyl]-5-ethyl-10,11-dihydro-5H-dibenz[b,f]azepine-10-carbonitrile.

H. To 10 parts of 10-[2-(dimethylamino)ethyl]-5-ethyl-10,11-dihydro-5H-dibenz[b,f]azepine-10-carbonitrile dissolved in a minimal amount of anhydrous ether is added just sufficient approximately 20% hydrogen chloride dissolved in 2-propanol to induce acidity. The precipitate which forms is collected on a filter, washed thereon with anhydrous ether, and dried in air. The light yellow powder thus isolated is 10[2-(dimethylamino)ethyl]-5-ethyl-10,11-dihydro-5H-dibenz[b,f]azepine-10-carbonitrile hydrochloride which, recrystallized from ethanol, melts at 243°–246°.

EXAMPLE 2

A. To a mixture of 3 parts of 5-ethyl-10,11-dihydro-5H-dibenz[b,f]azepine-10-carbonitrile with approximately 30 parts of tetrahydrofuran and 5 parts of N,N-dimethylformamide is added 6 parts of sodium hydride, followed by 3 parts of 2-chloro-N,N-diethylethanamine hydrochloride. The resultant mixture is heated at the boiling point under reflux with stirring while thin layer chromatography is employed to monitor the reaction which ensues, additional sodium hydride being introduced as indicated thereby. After approximately 3 hours, when no 5-ethyl-10,11-dihydro-5H-dibenz[b,f]azepine-10-carbonitrile is detectable, excess sodium hydride is destroyed by adding water until evolution of hydrogen ceases, whereupon solvent is removed by vacuum distillation. The residue is partitioned between ether and water. The ethereal phase, dried over magnesium sulfate and stripped of solvent by vacuum distillation, affords 10-[2-(diethylamino)ethyl]-5-ethyl-10,11-dihydro-5H-dibenz[b,f]azepine-l-carbonitrile as a clear yellow oil.

B. A solution of 10 parts of 10-[2-(diethylamino)ethyl]-5-ethyl-10,11-dihydro-5H-dibenz[b,f]azepine-10-carbonitrile in a minimal amount of 2-propanol is acidified with approximately 20% hydrogen chloride dissolved in 2-propanol. Precipitation occurs. Sufficient anhydrous ether is introduced to ensure completion of the precipitation, whereupon the insoluble solids are filtered off, washed with anhydrous ether, dried in air, and recrystallized from absolute ethanol to give 10-[2-(diethylamino)ethyl]-5-ethyl-10,11-dihydro-5H-dibenz[b,f]azepine-10-carbonitrile hydrochloride as a colorless solid melting at 211°–214°.

EXAMPLE 3

A. A solution of approximately 15 parts of 5-ethyl-10,11-dihydro-5H-dibenz[b,f]azepine-10-carbonitrile in 125 parts of tetrahydrofuran is added to 3 parts of a 57% dispersion of sodium hydride in white oil. The resultant mixture is stirred at around 50° for ½ hour, whereupon approximately 11 parts of 2-chloro-N,N-diisopropylethanamine is mixed in. The mixture thus obtained is heated at the boiling point under reflux with stirring while thin layer chromatography is employed to monitor the reaction which ensues, additional sodium hydride being introduced as indicated thereby. Reflux with stirring is continued overnight, whereupon excess sodium hydride is destroyed by adding water and the reaction mixture then extracted with ether. The extract is dried over magnesium sulfate and stripped of solvent by vacuum distillation. The residue is 10-[2-(diisopropylamino)ethyl]-5-ethyl-10,11-dihydro-5H-dibenz[b,f]azepine-10-carbonitrile.

B. A solution of 28 parts of 10-[2-diisopropylamino)ethyl]-5-ethyl-10,11-dihydro-5H-dibenz[b,f]azepine-10-carbonitrile in a minimal amount of anhydrous ether is acidified with a 20% solution of hydrogen chloride in anhydrous ether. The white solid which precipitates is filtered off, dried in vacuo at 60°–70°, and then recrystallized from absolute ethanol to give 10-[2-(diisopropylamino)ethyl]-5-ethyl-10,11-dihydro-5 H-dibenz[b,f]azepine-10-carbonitrile hydrochloride melting at 230°–233°.

EXAMPLE 4

A. To a solution of 10 parts of 5-ethyl-10,11-dihydro-5H-dibenz[b,f]azepine-10-carbonitrile in 90 parts of tetrahydrofuran and 10 parts of N,N-dimethylformamide is added 14 parts of a 57% dispersion of sodium hydride in white oil, followed — portionwise during ½ hour — by 10 parts of 3-chloro-N,N-dimethylpropanamine hydrochloride. The resultant mixture is heated at the boiling point under reflux with stirring for approximately 4 hours. At that point, no more 5-ethyl-10,11-dihydro-5H-dibenz[b,f]azepine-10-carbonitrile being detectable via thin layer chromatography, excess dodium hydride is destroyed by the addition of water and the resultant mixture is stripped of solvent by vacuum distillation. The residue is partitioned between ether and water. The ethereal phase is dried over magnesium sulfate and stripped of solvent by vacuum distillation. The residual oil is 10-[3-dimethylamino)-propyl]-5-ethyl-10,11-dihydro-5H-dibenz[b,f]azepine-10-carbonitrile.

B. Approximately 5 parts of 10-[3-(dimethylamino)-propyl]-5-ethyl-10,11-dihydro-5H-dibenz[b,f]azepine-10-carbonitrile is dissolved in minimal 2-propanol and the solution made acid with 20% hydrogen chloride in 2-propanol. A white solid precipitates. Sufficient anhydrous ether is added to insure completion of precipitation, whereupon the solids are filtered out, washed with anhydrous ether, dried in air, and recrystallized from a mixture of absolute ethanol and anhydrous ether to give 10-[3-(dimethylamino)propyl]-5-ethyl-10,11-dihydro-5H-dibenz[b,f]azepine-10-carbonitrile hydrochloride which, dried in vacuo, melts at 220.5°–222°.

EXAMPLe 5

A. To a solution of 15 parts of 5-ethyl-10,11-dihydro-5H-dibenz[b,f]azepine-10-carbonitrile in a mixture of 135 parts of tetrahydrofuran and 15 parts of N,N-dimethylformamide is added 14 parts of a 57% dispersion of sodium hydride, followed by 15 parts of N-benzyl-2-chloro-N-methylethanamine hydrochloride. The resultant mixture is heated at the boiling point under reflux with stirring overnight, thin layer chromatography being employed to monitor the reaction which ensues and additional sodium hydride in oil being introduced as indicated thereby. When no further 5-ethyl-10,11-dihydro-5H-dibenz[b,f]azepine-10-carbonitrile is detectable, excess sodium hydride is destroyed by adding water; and the resultant mixture is stripped of solvent by vacuum distillation. The residue is partitioned between ether and water. The ethereal phase is acidified with 20% hydrogen chloride in 2-propanol, whereupon supernatant liquors are decanted from the thick paste thrown down. The paste is mixed with approximately 500 parts of water, and this mixture is made alkaline with aqueous 50% sodium hydroxide. The mixture thus obtained is extracted with ether. The ether extract is dried over magnesium sulfate and stripped of solvent by vacuum distillation. The residual oil is 10-[2-(N-benzyl-N-methylamino)ethyl]-5-ethyl-10,11-dihydro-5H-dibenz[b,f]azepine-10-carbonitrile.

B. To a solution of 3 parts of 10-[2-(N-benzyl-N-methylamino)ethyl]-5-ethyl-10,11-dihydro-5H-dibenz[b,f]-azepine-10-carbonitrile in a minimal quantity of anhydrous ether is added just sufficient hydrogen chloride q.s. 20% in 2-propanol to induce acidity. The solid which precipitates is isolated by filtration, washed with anhydrous ether, and dried in vacuo. The product thus obtained is 10-[2-(N-benzyl-N-methylamino)ethyl]-5-ethyl-10,11-dihydro-5H-dibenz[b,f]azepine-10-carbonitrile hydrochloride.

EXAMPLE 6

Substitution of 16 parts of N-benzyl-2-chloro-N-ethylethanamine hydrochloride for the N-benzyl-2-chloro-N-methylethanamine hydrochloride called for in Example 5A affords, by the procedure there detailed, 10-[2-(N-benzyl-N-ethylamino)ethyl]-5-ethyl-10,11-dihydro-5H-dibenz[b,f]azepine-10-carbonitrile.

EXAMPLE 7

A solution of 49 parts of 10-[2-(dimethylamino)-ethyl]-5-ethyl-10,11-dihydro-5H-dibenz[b,f]azepine-10-carbonitrile in 120 parts of ethanol is added to a solution of 90 parts of potassium hydroxide in a mixture of 200 parts of ethanol with 10 parts of water. The resultant solution is heated at the boiling point under reflux with stirring for 23 hours, then cooled to room temperature and thereupon poured into 1,500 parts of a mixture of ice and water. The oil which separates is extracted into ether, which is removed by vacuum distillation. The residue is taken up in chloroform, and the chloroform solution is dried over magnesium sulfate and then stripped of solvent by vacuum distillation. The residual oil is crystallized from a mixture of ethyl acetate and hexane, thus affording 10[2-(dimethylamino)ethyl]-5-ethyl-10,11-dihydro-5H-dibenz[b,-f]azepine-10-carboxamide as a colorless solid melting at 148.5°–151°.

EXAMPLE 8

A mixture of 46 parts of 10-[2-(dimethylamino)ethyl]-5-ethyl-10,11-dihydro-5H-dibenz[b,f]azepine-10-carbonitrile and approximately 850 parts of concentrated sulfuric acid is heated at 90°–95° for ½ hour, then poured onto 2,500 parts of ice. The resultant mixture is made basic by the addition of aqueous 50% sodium hydroxide. The mixture thus obtained is extracted with ether. The ether extract is washed with water, dried over magnesium sulfate, and stripped of solvent by vacuum distillation. The residual clear yellow-brown oil is crystallized from hexane to give 10-[2-(diethylamino)ethyl]-5-ethyl-10,11-dihydro-5H-dibenz[b,f]azepine-10-carboxamide as a colorless solid melting at 95°–97°.

EXAMPLE 9

A mixture of 4 parts of 10-[2-(diisopropylamino)-ethyl]-5-ethyl-10,11-dihydro-5H-dibenz[b,f]azepine-10-carbonitrile and approximately 75 parts of concentrated sulfuric acid is heated at 90°–95° for 1 ½ hours, then poured onto 250 parts of ice. The resultant mixture is made basic via the addition of aqueous 50% sodium hydroxide. The mixture thus obtained is extracted with ether. The ether extract is washed with water, dried over magnesium sulfate, and stripped of solvent by vacuum distillation. The residual oil is crystallized from hexane. The colorless product thus isolated is 10-[2-(diisopropylamino)ethyl]-5-ethyl-10,11-dihydro-5H-dibenz[b,f]azepine-10-carboxamide melting at 101.5°–105.5°.

EXAMPLE 10

A. A solution of 26 parts of 10-[3-(dimethylamino)-propyl]-5-ethyl-10,11-dihydro-5H-dibenz[b,f]azepine-10-carbonitrile and 50 parts of potassium hydroxide in 105 parts of ethanol and 5 parts of water is heated at the boiling point under reflux with stirring. Thin layer chromatography, with alumina as the adsorbant and 9% methanol in ethyl acetate as the developing solvent, is used to monitor the reaction which ensues. When 10-[3-dimethylamino)propyl]-5-ethyl-10,11-dihydro-5H-dibenz[b,f]azepine-10-carbonitrile is no longer detectable (typically, after 22 hours), the reaction mixture is cooled to room temperature and then poured into 800 parts of water. The oil which separates is extracted with ether. The ether extract is washed with water, dried over magnesium sulfate, and stripped of solvent by vacuum distillation. The residual clear oil is 10-[3-(dimethylamino)propyl]-5-ethyl-10,11-dihydro-5H-dibenz[b,f]azepine-10-carboxamide.

B. To a solution of 11 parts of 10-[3-(dimethylamino)propyl]-5-ethyl-10,11-dihydro-5H-dibenz[b,f]azepine-10-carboxamide in a minimum amount of 2-propanol is added a solution of 3 parts of oxalic acid in 12 parts of 2-propanol. The resultant solution is diluted with sufficient anhydrous ether to induce formation of a solid precipitate. The precipitate is filtered off, washed with anhydrous ether, dried in vacuo, and taken up in 800 parts of methanol. The methanol solution is diluted with 10 parts of ethyl acetate, and the resultant solution is concentrated by vacuum distillation until most of the methanol is removed. The concentrate is cooled to room temperature, then diluted with just sufficient anhydrous ether to induce cloudiness, followed by just sufficient methanol to induce clarification. On refrigeration, 10-[3-(dimethylamino)propyl]-5-ethyl-10,11-dihydro-5H-dibenz[b,f]azepine-10-carboxamide hemioxalate separates as a yellowish crystalline precipitate. The product is isolated by filtration and dried in vacuo.

EXAMPLE 11

A. A mixture of 104 parts of 10-[2-(N-benzyl-N-methylamino)ethyl]-5-ethyl-10,11-dihydro-5H-dibenz[b,f]-azepine-10-carbonitrile and 169 parts of potassium hydroxide in 360 parts of ethanol and 15 parts of water is heated at the boiling point under reflux with stirring overnight. The reaction mixture is then poured into approximately 800 parts of ice water, and the resultant mixture is extracted with ether. The ether extract is washed with water, dried over magnesium sulfate, and stripped of solvent by vacuum distillation. The residual clear oil is 10-[2-(N-benzyl-N-methylamino)ethyl]-5-ethyl-10,11-dihydro-5H-dibenz[b,f]-azepine-10-carboxamide.

B. To a solution of 6 parts of 10-[2-(N-benzyl-N-methylamino)ethyl]-5-ethyl-10,11-dihydro-5H-dibenz[b,f]-azepine-10-carboxamide in a minimal amount of 2-propanol is added a solution of approximately 2 parts of oxalic acid in 10 parts of 2-propanol. Sufficient ether is thereupon added to induce precipitation. The precipitate is filtered out, washed with ether, dried in air, and taken up in 50 parts of methanol. To this solution is added 5 parts of ethyl acetate. The resultant solution is concentrated by vacuum distillation until most of the solvent is removed. The concentrate thus obtained is diluted with just sufficient 65% dichloromethane in ether to induce turbidity, followed by the minimum amount of methanol necessary to restore clarity. Upon refrigeration, precipitation occurs. The precipitate is filtered off and dried in vacuo. The yellowish-tan powder thus isolated is 10-[2-(N-benzyl-N-methylamino)ethyl]-5-ethyl-10,11-dihydro-5H-dibenz[b,f]-azepine-10-carboxamide oxalate.

EXAMPLE 12

A mixture of 1 part of 10% palladium-on-carbon with a solution of 10 parts of 10-[2-(N-benzyl-N-methylamino)ethyl]-5-ethyl-10,11-dihydro-5H-dibenz[b,f]azepine-10-carboxamide in 200 parts of ethanol is hydrogenated at an initial pressure of 60 lbs. per square inch. When the drop in pressure shows that debenzylation is complete, the catalyst is filtered out; and solvent is removed from the filtrate by vacuum distillation. The residual oil is 5-ethyl-10-[2-(methylamino)ethyl]-10,11-dihydro-5H-dibenz[b,f]azepine-10-carboxamide.

EXAMPLE 13

Substitution of 10 parts of 10-[2-(N-benzyl-N-ethylamino)ethyl]-5-ethyl-10,11-dihydro-5H-dibenz[b,f]azepine-10-carbonitrile for the 10-[2-(N-benzyl-N-methylamino)ethyl]-5-ethyl-10,11-dihydro-5H-dibenz[b,f]azepine-10-carboxamide called for in Example 12 affords, by the procedure there detailed, 5-ethyl-10-[2-(ethylamino)ethyl]-10,11-dihydro-5H-dibenz[b,f]azepine-10-carbonitrile.

EXAMPLE 14

Substitution of 100 parts of 5-ethyl-10-[2-(ethylamino)ethyl]-10,11-dihydro-5H-dibenz[b,f]azepine-10-carbonitrile for the 10-[2-(N-benzyl-N-methylamino)ethyl]-5-ethyl-10,11-dihydro-5H-dibenz[b,f]azepine-10-carbonitrile called for in Example 11A affords, by the procedure there detailed, 5-ethyl-10-[2-(ethylamino)ethyl]-10,11-dihydro-5H-dibenz[b,f]azepine-10-carboxamide.

EXAMPLE 15

A. To a solution of aluminum hydride at 0° prepared from 9 parts of concentrated sulfuric acid and 30 parts of approximately 4% lithium tetrahydroaluminate(1-) in accordance with the procedure of Brown and Yoon, loc. cit., is added a solution of 4 parts of 10-[2-(diethylamino)ethyl]-5-ethyl-10,11-dihydro-5H-dibenz[b,f]azepine-10-carbonitrile in 35 parts of tetrahydrofuran. The resultant mixture is stirred at room temperatures for 2 hours, then cooled to around 5° and maintained thereat while a solution of 2 parts of water in 4 parts of tetrahydrofuran, followed by 3 parts of aqueous 25% sodium hydroxide and then 3 parts of water are introduced. Insoluble solids are filtered out and washed with tetrahydrofuran. The washings and filtrate are combined, dried over magnesium sulfate, and stripped of solvent by vacuum distillation. The residual clear oil is 10-(aminomethyl)-N,N,5-triethyl-10,11-dihydro-5H-dibenz[b,f]azepine-10-ethanamine.

B. A solution of 4 parts of 10-(aminomethyl)-N,N,5-triethyl-10,11-dihydro-5H-dibenz[b,f]azepine-10-ethanamine in a minimal quantity of absolute ethanol is acidified with a 15% solution of hydrogen bromide in ethanol. Sufficient anhydrous ether is then added to induce separation of an oil. Supernatant solvents are decanted from the oil, which is crystallized by slurrying with anhydrous ether. The product thus isolated, filtered off and recrystallized from a mixture of ethanol and absolute ether, affords 10-(aminomethyl)-N,N,5-triethyl-10,11-dihydro-5H-dibenz[b,f]azepine-10-ethanamine dihydrobromide as a colorless solid which, dried in vacuo at 80°, melts at 234°–236°.

EXAMPLE 16

A. Substitution of 4 parts of 10-[2-(diisopropylamino)ethyl]-5-ethyl-10,11-dihydro-5H-dibenz[b,f]azepine-10-carbonitrile for the 10-[2-(diethylamino)ethyl]-5-ethyl-10,11-dihydro-5H-dibenz[b,f]azepine-10-carbonitrile called for in Example 15A affords, by the procedure there detailed, 10-(aminomethyl)-5-ethyl-10,11-dihydro-N,N-diisopropyl-5H-dibenz[b,f]azepine-10-ethanamine as a clear yellow oil.

B. A solution of 4 parts of 10-(aminomethyl)-5-ethyl-10,11-dihydro-N,N-diisopropyl-5H-dibenz[b,f]azepine-10-ethanamine in a minimal amount of absolute ethanol at around 20° is acidified with a 15% solution of hydrogen bromide in ethanol. Sufficient ether is added to cause an oil to separate. Supernatant solvents are decanted from the oil, which is crystallized by slurrying with anhydrous ether. Recrystallization from absolute ethanol affords 10-(aminomethyl)-5-ethyl-10,11-dihydro-N,N-diisopropyl-5H-dibenz[b,f]azepine-10-ethanamine dihydrobromide as a colorless solid which, washed with anhydrous ether and dried in vacuo at 80°, melts at approximately 239°–240°.

EXAMPLE 17

Substitution of 4 parts of 5-ethyl-10-[2-(ethylamino)ethyl]-10,11-dihydro-5H-dibenz[b,f]azepine-10-carbonitrile for the 10-[2-diethylamino)ethyl]-5-ethyl-10,11-dihydro-5H-dibenz[b,f]azepine-10-carbonitrile called for in Example 15A affords, by the procedure there detailed, 10-(aminomethyl)-N,5-diethyl-10,11-dihydro-5H-dibenz[b,f]azepine-10-ethanamine.

EXAMPLE 18

A. To a suspension of 50 parts of 5H-dibenz[b,f]azepine in 700 parts of dichloromethane is slowly added, with stirring, a solution of 65 parts of ethyl chloroformate in 125 parts of dichloromethane. The resultant mixture is heated at the boiling point under reflux with stirring for 24 hours, then consecutively cooled to room temperature, washed with aqueous 5% sodium hydroxide followed by 5% hydrochloric acid and finally by water, dried over magnesium sulfate, and stripped of solvent by vacuum distillation. The residue is ethyl 5H-dibenz[b,f]azepine-5-carboxylate.

B. To a solution of 106 parts of ethyl 5H-dibenz[b,f]azepine-5-carboxylate in 750 parts of chloroform at around 0° is slowly added, with stirring, a solution of 64 parts of bromine in 150 parts of chloroform. When the addition is complete, the resultant mixture is stirred at room temperatures for 2 hours, whereupon solvent is removed by vacuum distillation. The residue is ethyl 10,11-dibromo-10,11-dihydro-5H-dibenz[b,f]azepine-5-carboxylate.

C. A mixture of 57 parts of ethyl 10,11-dibromo-10,11-dihydro-5H-dibenz[b,f]azepine-5-carboxylate and 60 parts of N-butylbutanamine is heated at 90°–95° for 2 hours, then cooled to room temperature and extracted with ether. The ether extract is washed with sufficient 5% hydrochloric acid that the wash remains acidic, whereupon it is washed with water, dried over magnesium sulfate, and stripped of solvent by vacuum distillation. The residue is ethyl 10-bromo-5H-dibenz[b,f]azepine-5-carboxylate.

D. To 275 parts of a 3 ½% solution of lithium aluminate(1-) in tetrahydrofuran at 0°–5° is slowly added, with vigorous stirring, 15 parts of concentrated sulfuric acid. The resultant mixture is stirred at 0°–5° for 1 hour, whereupon a solution of 34 parts of ethyl 10-bromo-5H-dibenz[b,f]azepine-5-carboxylate in 225 parts of tetrahydrofuran is introduced. The mixture thus obtained is stirred for 1 hour, whereupon a solution of 20 parts of water in 40 parts of tetrahydrofuran, followed by 30 parts of aqueous 25% sodium hydroxide and then finally by 30 parts of water, is added. Insoluble solids are filtered out and washed with several portions of tetrahydrofuran. Washings and filtrate are combined, dried over magnesium sulfate, and stripped of solvent by vacuum distillation to give 10-bromo-5-methyl-5H-dibenz[b,f]azepine as the residue.

E. A mixture of 18 parts of 10-bromo-5-methyl-5H-dibenz[b,f]azepine, 11 parts of copper(I) cyanide, and 200 parts of N,N-dimethylformamide is heated at the boiling point under reflux with stirring for 1 hour, then cooled to room temperature and thereupon poured into 900 parts of concentrated ammonium hydroxide. The resultant mixture is extracted with dichloromethane. The dichloromethane extract is dried over magnesium sulfate and stripped of solvent by vacuum distillation. The residue is 5-methyl-5H-dibenz[b,f]azepine-10-carbonitrile.

F. To a solution of 70 parts of 5-methyl-5H-dibenz[b,f]azepine-10-carbonitrile in 2,500 parts of methanol is added, portionwise during 15 minutes, 115 parts of sodium tetrahydroborate(1-). Heat is evolved. The reaction mixture is stirred until it cools to room temperature, whereupon solvent is removed by vacuum distillation and the residue partitioned between ether and water. The ethereal phase is washed with water, dried over magnesium sulfate, and stripped of solvent by vacuum distillation. The residue is 10,11-dihydro-5-methyl-5-H-dibenz[b,f]azepine-10-carbonitrile.

G. Substitution of 14 parts of 10,11-dihydro-5-methyl-5H-dibenz[b,f]azepine-10-carbonitrile and 11 parts of 3-chloro-N,N-dimethylpropanimine hydrochloride for the 5-ethyl-10,11-dihydro-5H-dibenz[b,f]azepine-10-carbonitrile and N-benzyl-2-chloro-N-methylethanamine hydrochloride, respectively, called for in Example 5A affords, by the procedure there detailed, 10-[3-(dimethylamino)propyl]-10,11-dihydro-5-methyl-5H-dibenz[b,f]azepine-10-carbonitrile.

EXAMPLE 19

Substitution of 87 parts of 10-[3-(dimethylamino)propyl]-10,11-dihydro-5-methyl-5H-dibenz[b,f]azepine-10-carbonitrile for the 10-[2-(N-benzyl-N-methylamino)ethyl]-5-ethyl-10,11-dihydro-5H-dibenz[b,f]azepine-10-carbonitrile called for in Example 11A affords, by the procedure there detailed, 10-[3-(dimethylamino)propyl]-10,11-dihydro-5-methyl-5H-dibenz[b,f]azepine-10-carboxamide.

EXAMPLE 20

Substitution of 4 parts of 10-[3-(dimethylamino)propyl]-10,11-dihydro-5-methyl-5H-dibenz[b,f]azepine-10-carbonitrile for the 10-[2-(diethylamino)ethyl]-5-ethyl-10,11-dihydro-5H-dibenz[b,f]azepine-10-carbonitrile called for in Example 15A affords, by the procedure there detailed, 10-aminomethyl) N,N-dimethyl-10,11-dihydro-5-methyl-5H-dibenz[b,f]azepine-10-propanamine.

What is claimed is:

1. A compound of the formula

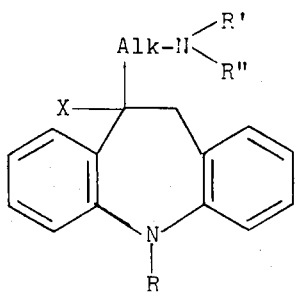

wherein X represents aminocarbonyl aminomethyl, or cyano; Alk represents alkylene containing two or three carbons; R and R' each represent alkyl containing fewer than eight carbons; and R" represents hydrogen, alkyl containing fewer than eight carbons, or benzyl.

2. A compound according to claim 1 having the formula

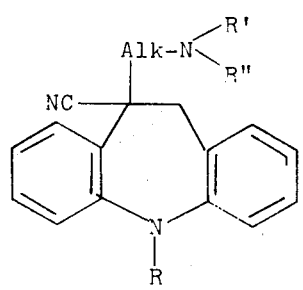

wherein Alk represents alkylene containing two or three carbons; R and R' each represent alkyl containing fewer than eight carbons; and R" represents hydrogen, alkyl containing fewer than eight carbons, or benzyl.

3. A compound according to claim 1 having the formula

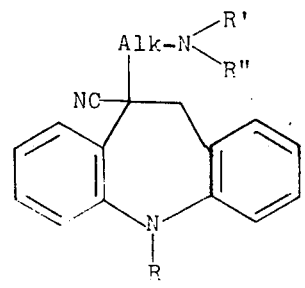

wherein Alk represents alkylene containing two or three carbons and R, R', and R" each represent alkyl containing fewer than eight carbons.

4. A compound according to claim 1 having the formula

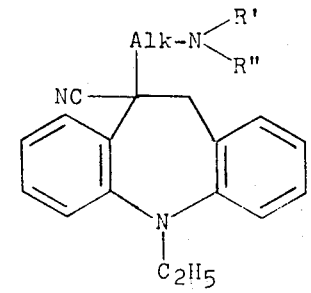

in which Alk represents alkylene containing two or three carbons and R' and R" each represent alkyl containing fewer than eight carbons.

5. A compound according to claim 1 which is 10-[2-(diisopropylamino)ethyl]-5-ethyl-10,11-dihydro-5H-dibenz[b,f]azepine-10-carbonitrile.

6. A compound according to claim 1 which is 10-[3-(dimethylamino)propyl]-5-ethyl-10,11-dihydro-5H-dibenz[b,f]azepine-10-carbonitrile.

7. A compound according to claim 1 having the formula

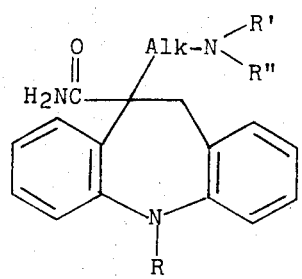

wherein Alk represents alkylene containing more than one and fewer than four carbons; R and R' each represent alkyl containing fewer than eight carbons; and R" represents hydrogen, alkyl containing fewer than eight carbons, or benzyl.

8. A compound according to claim 1 which is 10-[2-(N-benzyl-N-methyl)ethyl]-5-ethyl-10,11-dihydro-5H-dibenz[b,f]azepine-10-carboxamide.

9. A compound according to claim 1 having the formula

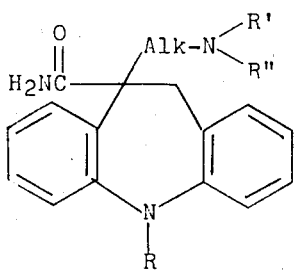

wherein Alk represents alkylene containing two or three carbons and R, R', and R" each represent alkyl containing fewer than eight carbons.

10. A compound according to claim 1 having the formula

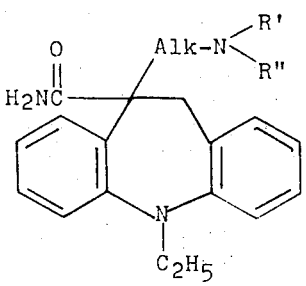

wherein Alk represents alkylene containing two or three carbons and R' and R" each represent alkyl containing fewer than eight carbons.

11. A compound according to claim 1 which is 10-[3-(dimethylamino)propyl]-5-ethyl-10,11-dihydro-5H-dibenz[b,f]azepine-10-carboxamide.

12. A compound according to claim 1 having the formula

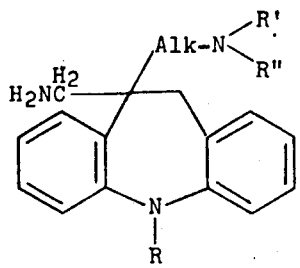

wherein Alk represents alkylene containing two or three carbons, R and R' each represent alkyl containing fewer than eight carbons, and R' represents hydrogen or alkyl containing fewer than eight carbons.

13. A compound according to claim 1 having the formula

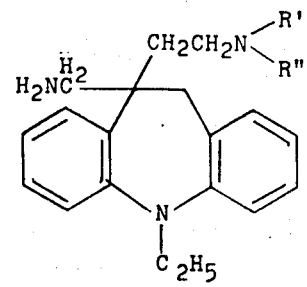

wherein R' and R" each represent alkyl containing fewer than eight carbons.

14. A compound according to claim 1 which is 10-(aminomethyl)-5-ethyl-10,11-dihydro-N,N-diisopropyl-5H-dibenz[b,f]azepine-10-ethanamine.

15. 5-Ethyl-10,11-dihydro-5H-dibenz[b,f]azepine-10-carbonitrile.

* * * * *

UNITED STATES PATENT OFFICE
CERTIFICATE OF CORRECTION

Patent No. 3,985,730         Dated October 12, 1976

Inventor(s) John W. Cusic et al.

It is certified that error appears in the above-identified patent and that said Letters Patent are hereby corrected as shown below:

On the Title Page, Item [54] should read:

--- 5-ALKYL-10-(AMINOCARBONYL/AMINOMETHYL/CYANO)-10,11-DIHYDRO-5H-DIBENZ[b,f]AZEPINE-10-ALKANAMINES ---.

Signed and Sealed this

Twenty-first Day of December 1976

[SEAL]

Attest:

RUTH C. MASON
*Attesting Officer*

C. MARSHALL DANN
*Commissioner of Patents and Trademarks*

UNITED STATES PATENT AND TRADEMARK OFFICE
CERTIFICATE OF CORRECTION

PATENT NO. : 3,985,730
DATED : Oct. 12, 1976
INVENTOR(S) : John W. Cusic and Charles R. Ellefson It is certified that error appears in the above-identified patent and that said Letters Patent are hereby corrected as shown below:

Column 3, line 67, "95%" should read -- ≯ 95% --.

Column 7, line 25, "conplete" should read -- complete --.

Column 7, line 45, "ensures" should read -- ensues --.

Column 9, line 10, "dodium" should read --sodium --.

Column 9, line 31, "EXAMPLe" should read -- EXAMPLE --.

Column 11, line 22, "800" should read -- 80 --.

Column 16, Claim 7, lines 27 and 28, "more than one and fewer than four" should read -- 2 or 3 --.

Signed and Sealed this

*Twenty-second* Day of *November 1977*

[SEAL]

Attest:

RUTH C. MASON
*Attesting Officer*

LUTRELLE F. PARKER
*Acting Commissioner of Patents and Trademarks*